(12) United States Patent
Sarvazyan et al.

(10) Patent No.: US 6,620,115 B2
(45) Date of Patent: Sep. 16, 2003

(54) APPARATUS AND METHOD FOR MECHANICAL IMAGING OF BREAST

(75) Inventors: Armen P. Sarvazyan, Lambertville, NJ (US); Vladimir Egorov, Plainsboro, NJ (US)

(73) Assignee: Armed L.L.C., Minneapolis, MN (US)

( * ) Notice: Subject to any disclaimer, the term of this patent is extended or adjusted under 35 U.S.C. 154(b) by 0 days.

(21) Appl. No.: 09/843,056

(22) Filed: Apr. 26, 2001

(65) Prior Publication Data

US 2002/0004630 A1 Jan. 10, 2002

Related U.S. Application Data

(60) Provisional application No. 60/200,433, filed on Apr. 28, 2000.

(51) Int. Cl.[7] .............................................. A61B 5/103
(52) U.S. Cl. ...................................................... 600/587
(58) Field of Search .................................. 600/587, 595

(56) References Cited

U.S. PATENT DOCUMENTS

| | | | |
|---|---|---|---|
| 4,250,894 A | | 2/1981 | Frei et al. |
| 4,657,021 A | | 4/1987 | Perry et al. |
| 4,793,354 A | | 12/1988 | Wright et al. |
| 5,099,848 A | | 3/1992 | Parker et al. |
| 5,107,837 A | | 4/1992 | Ophir et al. |
| 5,143,070 A | | 9/1992 | Ophir et al. |
| 5,178,147 A | | 1/1993 | Ophir et al. |
| 5,293,870 A | | 3/1994 | Ophir et al. |
| D348,618 S | | 7/1994 | Leslie et al. |
| 5,572,995 A | | 11/1996 | Rohrberg |
| 5,833,633 A | * | 11/1998 | Sarvazyan .................. 600/587 |
| 5,883,634 A | | 3/1999 | Narayanaswami |
| 5,989,199 A | | 11/1999 | Cundari et al. |

OTHER PUBLICATIONS

Kessler, L. Acoustical Imaging vol. 16, pp. 317–327, 1988, Sono–Elasticity: Medical Elasticity Images.

Oncology News Int'l., vol. 8, No. 2, 1999, Electronic Palpation Device Adjunct to Manual Breast Exam.

Krouskop, T. et al. Journal of Rehab. Research Vet. Admin. vo. 24, No.2, 1987, pp.–1–8,Pulse Doppler.

Yamakoshi, Y. et al. IEEE Transactions on Ultrasonics, vol. 37, No. 2 1990, pp.45–53 Ultrasonic Imaging.

Gentle Cr Mammobarograph a possible method of mass breast screening, J. Biomed Eng. 10, 124–26, 1988.

Oncology News Int'l. Electronic Palpation Mau Detect Breast Cancers, Feb., 1999.

Lerner, et al. Sono–Elasticity: Medical Elasticity Images Derived From Acoustical Imaging vo. 16, 317, 1988.

Krouskop et al. A Pulsed Doppler Ultrasonic System for Making Non–Invasive Measurements of Mechanical properties of soft tissue.

Yamakoshi et al., Ultrasonic Imaging of Internal Vibration, IEEE Transactions on Ultrasonics vol. 7, No. 2 p. 45, 1990.

Starck, et al., Image Processing and Data Analysis, Cambridge Univ. Press, 1998.

* cited by examiner

*Primary Examiner*—Max F. Hindenburg
*Assistant Examiner*—Pamela L Wingood
(74) *Attorney, Agent, or Firm*—Mathews, Collins, Shepherd & McKay, P.A.

(57) ABSTRACT

A method and device in accordance with the present invention enabling detecting mechanical and structural properties of the breast tissue that are indicative of breast cancer. Detection of nodules is achieved by placing the breast into a mechanical scanning unit comprising of a two-dimensional pressure sensor array and a mobile linear pressure sensor array located opposite to the two-dimensional pressure sensor array, and analyzing the signals from the pressure sensors. The device is able to objectively detect presence of lesions suspicious for cancer or other breast pathologies in the breast and provide means for computerized three-dimensional mechanical imaging of the breast.

11 Claims, 16 Drawing Sheets

APPARATUS AND METHOD FOR MECHANICAL IMAGING OF BREAST

This application claims the benefit of Provisional application No. 60/200,433, filed Apr. 28, 2000.

This invention was made with government support under SBIR Grants No. 1 R43 CA65246-01 At and No. 2 R44 CA69175-03 awarded by the National Institutes of Health, National Cancer Institute. The government has certain rights in this invention.

BACKGROUND OF THE INVENTION

1. Field of the Invention

The present invention relates to a method and apparatus for the computerized mechanical palpation of the breast and detecting changes in mechanical properties of the breast tissue that are indicative of breast cancer and other breast pathologies accompanied by changes in the tissue viscoelasticity.

2. Description of the Related Art

Breast cancer is a major source of cancer morbidity and mortality in women. Various techniques have been developed for early diagnosis of breast cancer including ultrasonic imaging, nuclear magnetic resonance imaging, x-rays, and the like. Currently, the most widely used clinical method of diagnosing breast cancer is mammography. Efforts to reduce mortality via screening mammography have been successful with improvement in survival, particularly in women over 50 years old. One of the major disadvantages of the use of mammography is patients' exposure to radiation.

One of the safest and oldest techniques of detecting tissue disease is manual palpation. Palpation encompasses examination using the sense of touch, and is based on the significant difference in elasticity of normal and diseased tissues. Overall, about two-thirds of cancers are detected by palpation. Such sensitivity is related to significant changes in mechanical properties of tissues in the course of breast cancer development. In the United States the technique of self-palpation is widely taught to women as an effective means of early cancer detection. A significant fraction of breast cancer is first detected by women themselves who find suspicious lesions within their breasts and bring the problem to the attention of their physicians. The main disadvantage of manual palpation is its high degree of subjectivity. The examiner has to instinctively relate what he or she perceives by the finger to his or her previous experience. Moreover, a physician performing the examination cannot objectively record the state of the examined breast.

A number of devices have been developed for detecting regions of hardening in the breast tissues. Several authors have proposed various devices for breast palpation using different types of force sensors, but all with limited success. For example, a device described by Gentle in Gentle CR, "Mammobarography: A Possible Method of Mass Breast Screening", I. Biomed. Eng. 10, 124–126, 1988 was capable of detecting 'lumps of 6 mm in diameter in breast phantoms but was unable to obtain any quantitative data on lumps in a human breast. Many of the proposed breast self examination means were related to simple non-computerized mechanical systems enhancing sense of touch such as apparatuses described in U.S. Pat. No. 5,572,995, U.S. Pat. No. 4,657,021, U.S. Pat. No. 4,793,354, and U.S. Pat. No. D348,618.

Various types of devices mimicking manual palpation for detecting breast tumors using different types of force sensors have been developed. For example, Frei et al., U.S. Pat. No. 4,250,894, describes an instrument which uses a number of piezoelectric strips pressed into the breast during the examination by a pressurizing unit which applies a given periodic or steady' stress to the tissue beneath the strips.

Another method and device for breast examination are described in the U.S. Pat. No. 5,883,634 and U.S. Pat. No. 5,989,199. The sensors used in this device are based on the force sensor array manufactured by Tekscan Inc., Boston, Mass. The array consists of conductive rows and columns whose intersecting points form sensing locations. A material, which changes its electrical resistance under applied force, separates the rows and columns. Thus, each intersection becomes a force sensor. Clinical data obtained using this device were published in February 1999 issue of the Oncology News International, in an article entitled "Electronic Palpation May Detect Breast Cancers". The device showed an overall sensitivity of 92% (detecting 108 of 118 palpable and nonpalpable lesions) vs. 86% for the physician's exams (102 of 118 lesions). The device correctly detected all eight palpable cancers found in the study population and two of three non-palpable cancers.

Conventional imaging modalities capable of detecting motion of a tissue subjected to an external force (such as ultrasound or MRI) use indirect means of evaluation for determining the elasticity of the tissues. One such approach is based on determining the relative stiffness or elasticity of the tissue by applying ultrasound imaging techniques while vibrating the tissue at low frequencies. See. e.g., K. I. Parker et al, U.S. Pat. No. 5,099,848; R. M. Lerner et al., *Sono-Elasticity: Medical Elasticity Images Derived From Ultrasound Signals in Mechanically Vibrated Targets*. Acoustical Imaging, Vol. 16, 317 (1988); T. A. Krouskop et al., *A Pulsed Doppler Ultrasonic* 241, *Rehab. Res. Dev.* Vol. 24, 1 (1987); and Y. Yamakoshi et al., *Ultrasonic Imaging of Internal Vibration of Soft Tissue Under Forced Vibration*, IEEE Transactions on Ultrasonics, Ferroelectrics, and Frequency Control, Vol. 7, No. 2, Page 45 (1990).

Another method proposed for measuring and imaging tissue elasticity is described in Ophir et al., U.S. Pat. Nos. 5,107,837, 5,293,870, 5,143,070 and 5,178,147. This method includes emitting ultrasonic waves into the tissue and detecting an echo sequence resulting from the ultrasonic wave pulse. The tissue is then compressed (or alternatively decompressed from a compressed state) along the path. During such compression a second pulse of ultrasonic waves is sent along the path into the tissue. The second echo sequence resulting from the second ultrasonic wave pulse is detected. Next, the differential displacement of the selected echo segments of the first and second echo sequences are measured. A selected echo segment of the echo sequence, i.e., reflected RF signal, corresponds to a particular echo source within the tissue along the beam axis of the transducer. Time shifts in the echo segment are examined to measure compressibility of various regions in the examined tissue.

All presently available methods of palpatory assessment of the breast are inferior to manual palpation in sensitivity and specificity. Therefore, further development of screening techniques with greater sensitivity, specificity and accuracy is urgently warranted. It is desirable to provide computerized palpation of the breast which is capable of detecting breast lesions with sensitivity and spatial resolution exceeding that of manual palpation for use in early diagnostics of breast cancer.

The invention will be more fully described by reference to the following drawings.

SUMMARY OF THE INVENTION

The present invention provides a device and method for detection of abnormalities in tissues accompanied by the changes in their elasticity (such as those caused by cancer). The method is based on a computerized mechanical imaging referred to herein as CMI. The essence of CMI is the reconstruction of the internal structure of the soft tissues in a human body by measuring a dynamic or oscillatory stress pattern using an array of pressure sensors. The pattern of the dynamic mechanical stress and its changes as a function of applied pressure and time contain comprehensive information on the mechanical properties and geometry of the internal structures of the studied tissues.

The CMI devices are applicable in those fields of medicine where palpation is proven to be a sensitive tool in detecting and monitoring diseases (including but not limited to the breast cancer.

In a preferred embodiment, the apparatus for mechanical imaging of the breast comprises an electronically controlled mechanical scanning unit with a number of pressure transducers and an electronic unit for data acquisition, processing and displaying of images. The mechanical scanning unit includes a compression mechanism, three-dimensional positioning system, and local pressure source with a linear pressure sensor array opposing a two-dimensional pressure sensor array. The local pressure source is either a roller that is moved over the examined breast or, in an alternate embodiment, a linear pressure sensor array which can be moved in three dimensions. The electronic unit receives the pressure data from the pressure transducers and the position data from the positioning system and determines the mechanical structure of the breast.

The apparatus of the current invention uses sensors based on piezoelectric films, such as piezopolymer polyvinylidene fluoride (PVDF) and comprises mechanical arrangements allowing increasing PVDF signal. The piezopolymer film provides inexpensive means for measuring mechanical forces by converting them into electrical signals.

In the method of the present invention, the position data and pressure response data are acquired for translational and oscillation displacement overlaying the breast by periodic pressing or oscillating the linear pressure sensor array attached to the slider pressed against the breast. A pattern of pressure responses, pressure gradient responses, and spectral characteristic of pressure responses are determined and used for generating a mechanical image of the breast.

The present invention utilizes the similar mechanical information as obtained by manual palpation conducted by a skilled physician but objectively and with higher sensitivity and accuracy. The essence of the proposed method and device is detection of tissue heterogeneity by measuring changes in the surface stress pattern using a force sensing array applied to the tissue in the oscillatory mode. Temporal and spatial changes of the spectral components and phase relationships of oscillatory signals from the sensors contain information on the mechanical properties and geometry of the internal structures of the breast. The device and method in accordance with the present invention enable the user to detect changes in the breast tissue that are indicative of cancer development.

The present invention expands on teachings of interrelation of mechanical heterogeneities in the tissue and respective changes in the measured stress patterns, and temporal and spatial derivatives of the oscillatory signals from the force sensors on the surface of the tissue. The present invention also expands on the teaching that the above relationship forms the basis for a method of detecting and quantifying tissue abnormalities.

With the foregoing and other objects, advantages and features of the invention that will become hereinafter apparent, the nature of the invention may be more clearly understood by referencing to the following detailed description of the invention, the appended claims and the several views illustrated in the drawing.

DETAILED DESCRIPTION OF THE INVENTION

Figure 1:
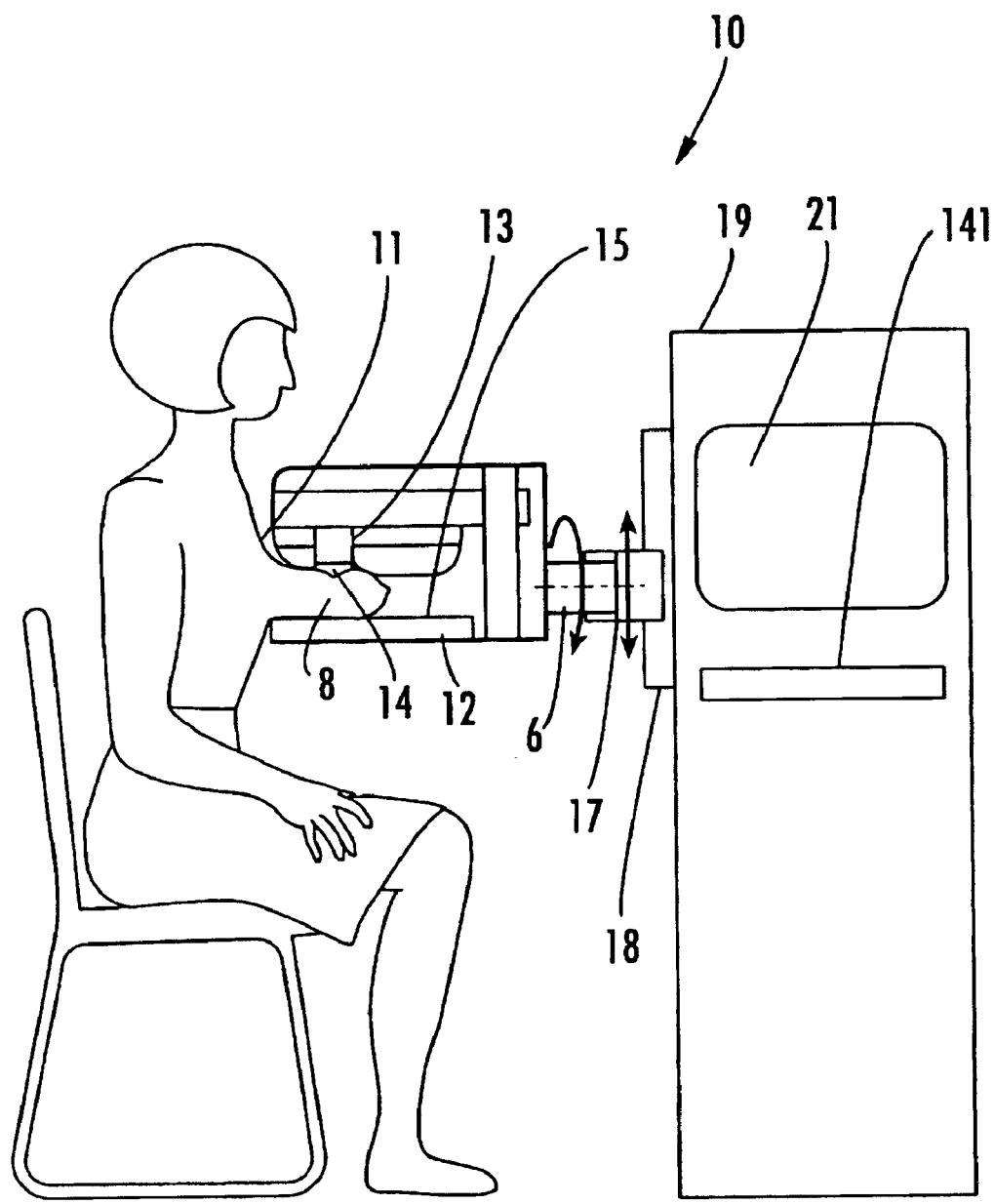
FIG. 1 is a cross-sectional side view of an embodiment of a mechanical scanning unit used with the pressure sensor array during breast examination.

References will be made in detail to a preferred embodiment of the invention, an example of which is illustrated in the accompanying drawings. Wherever possible, the same reference numerals will be used throughout the drawings and the description will refer to the same or similar parts.

An embodiment of the invention shown in FIGS. 1–4 is a clinical device for imaging the mechanical structure of the examined breast and diagnosing diseases accompanied by changes in the elasticity of the breast tissue. A perspective of the use of a device for mechanical imaging of the breast 10 of the present invention during breast examination is shown in FIG. 1. The patient sits in a chair so that the examined breast 8 is located and loosely inserted into the breast aperture 11. Such examination position allows the pectoral muscles to relax and the chest to expand into breast aperture 11 for greater access to the breast tissue adjacent to the chest wall. Inside breast aperture 11, breast 8 is placed and compressed between holder 12 and mechanical scanning unit 13. Holder 12 includes two-dimensional pressure sensor array 33 on an upper surface thereof. Mechanical scanning unit 13 includes linear pressure sensor array 14. Pressure transducers of two-dimensional pressure sensor array 33 and linear pressure sensor array 14 generate signals, which vary depending on the force applied to the breast tissue.

Device 10 also comprises an electronic unit (not shown), housing 19, electric power supply (not shown), computer display 20 and control unit 141. Revolving holder 16 is coupled to support 15. Positioning base 17 is coupled to housing 19. Revolving holder 16 is received in positioning base 17. Revolving holder 16 received in positioning base 17 can be rotated for rotating support 15 to allow holder 12 and mechanical scanning unit 13 to rotate along the horizontal axis. Revolving holder 16 received in positioning base 17 can move up and down along frame 18 connected to housing 19. The examination is monitored on computer display 20. Control unit 141 is intended for controlling the examination process, data analysis and data displaying.

Figure 2:
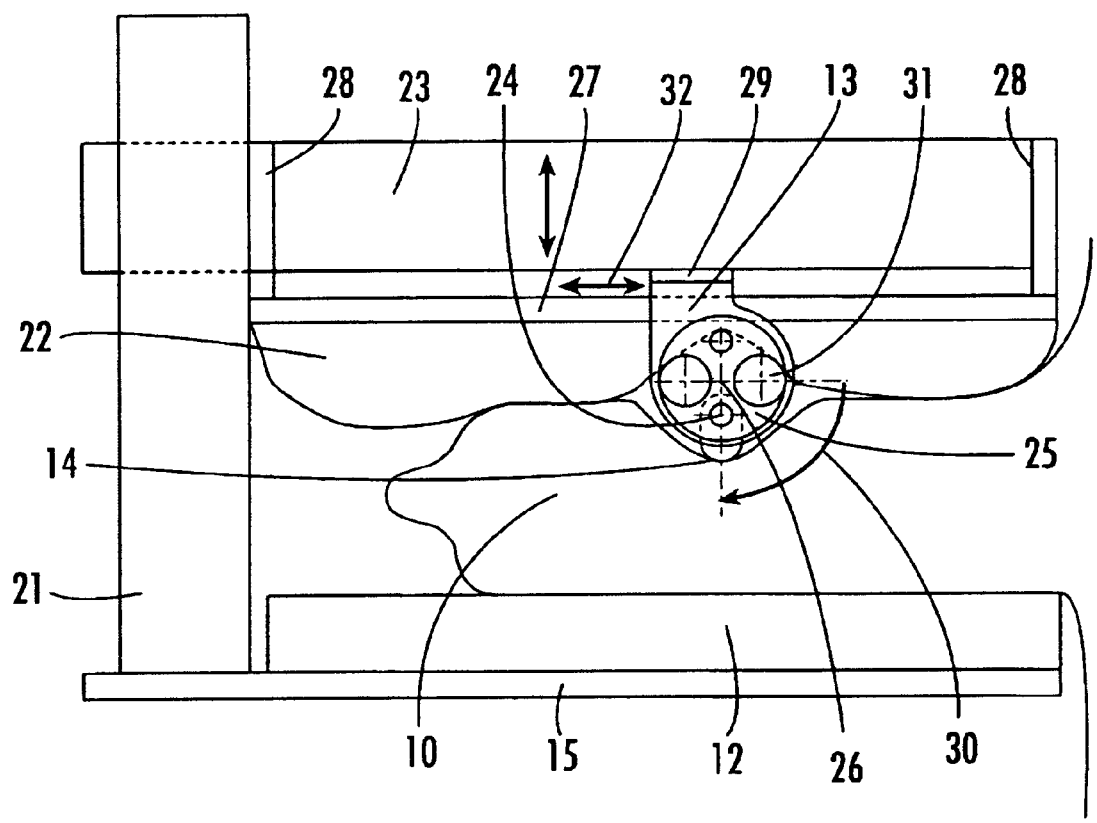
FIG. 2 is a detailed cross-sectional view of the mechanical scanning unit shown in FIG. 1 with a linear pressure sensor array and a two-dimensional pressure sensor array.

FIG. 2 shows a detailed cross-sectional view of a portion of device 10 including compression mechanism, robotic positioning system of the scanning unit and pressure sensor elements. Breast 8 is positioned adjacent air bag 22. Vertical linear actuator 21 and air bag 22 control the level of breast compression by means of elevating or lowering horizontal linear actuator 23 connected to slider (not shown) of vertical linear actuator 21 and by inflating air bag 22. Air bag 22 is secured on support 27. Support 27 is connected to horizontal linear actuator 23 by means of two corbels 28. Support 27 can be substantially flat. Linear pressure sensor array 14 extends from airbag 22 and is used, measures the level of the breast compression.

Figure 3:
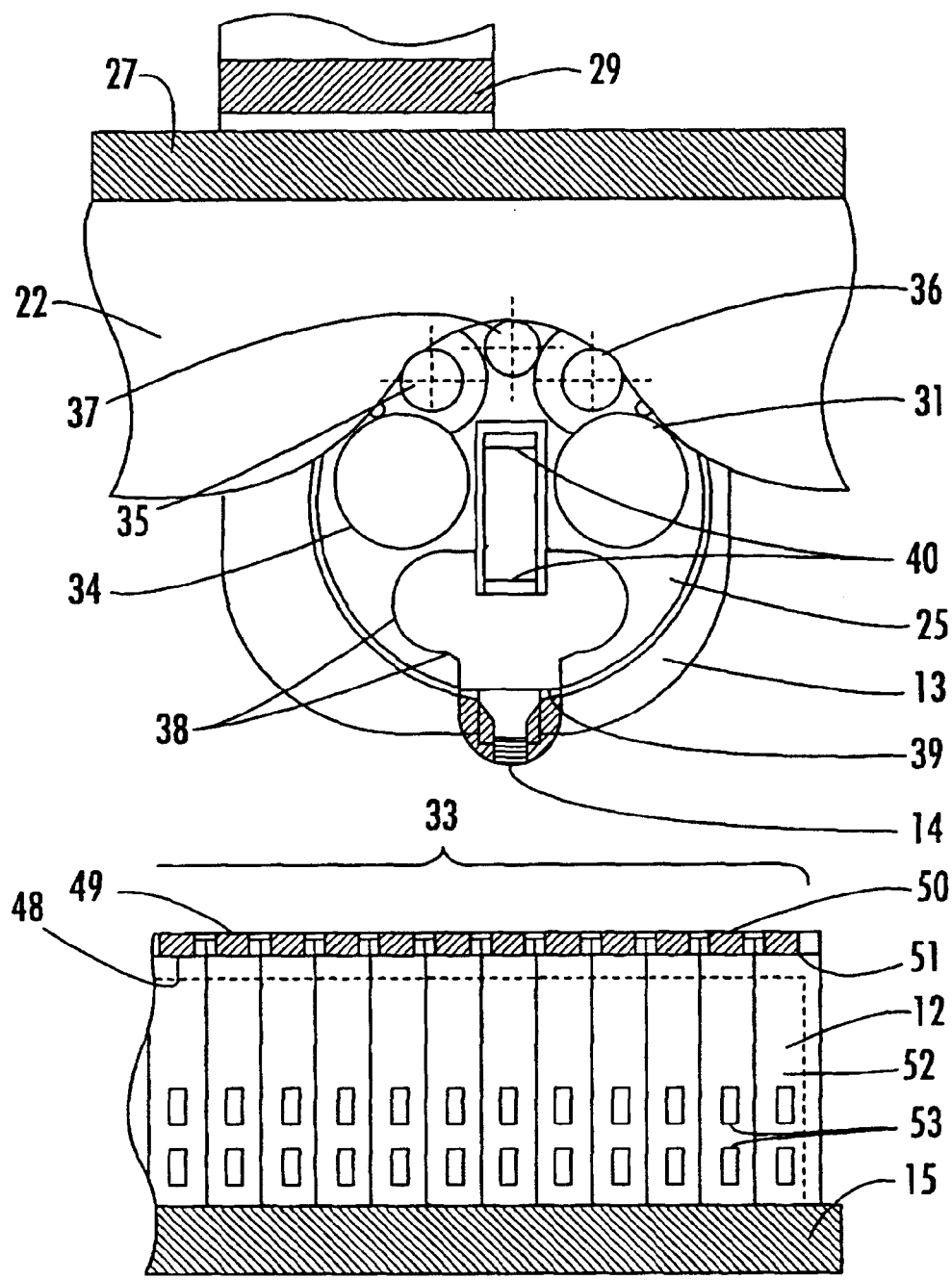
FIG. 3 is a detailed cross-sectional front view of the mechanical scanning unit shown in FIG. 1 for performing mechanical imaging of a breast in accordance with the present invention.
Figure 4:
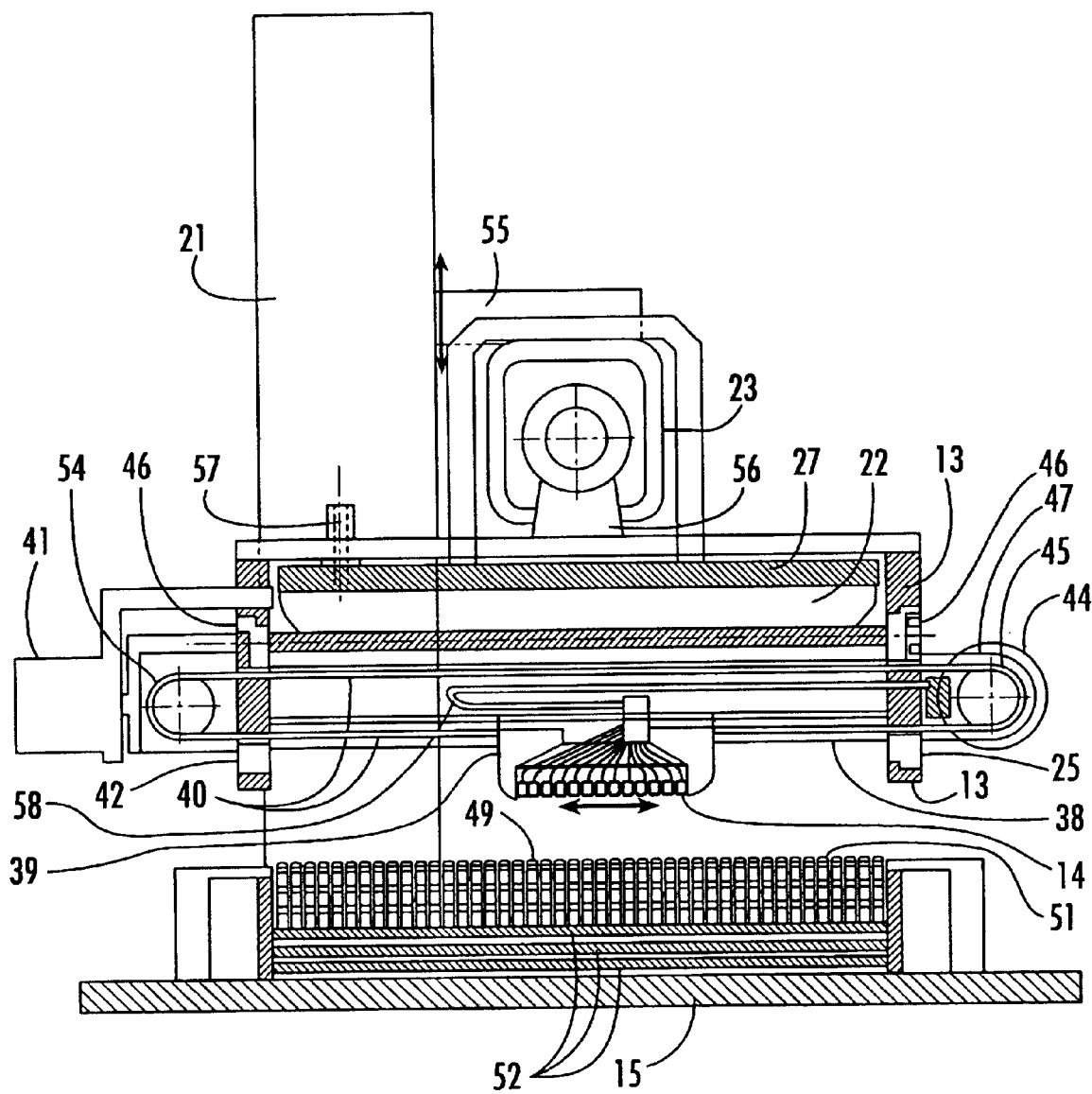
FIG. 4 is a schematic view of an apparatus for performing mechanical imaging of a breast in accordance with the present invention.

The robotic positioning system includes mechanical scanning unit 13 connected to slider 29 of horizontal linear actuator 23, linear pressure sensor array 14 which can move horizontally along axis 24 and rotary actuator 41, as shown in FIG. 4, for rotating rotation unit 25 relative to horizontal axis 26. Rotation unit 25 has two positions. The first position of rotation unit 25 is shown in FIG. 2 with linear pressure sensor array 14 contacting breast 8. This position is used for local examination of breast 8 in oscillation mode using back-and-forth motion of linear pressure sensor array 14 along axis 26. The second position of rotation unit 25 has rotation unit 25 rotated clockwise 90 degrees as shown by arrow 30. Roller 31 contacting breast 8 in the second position of rotation unit 25 is used for scanning the entire breast by means of linear motion of scanning unit 13 as shown by arrow 32. Movement out of roller 31 acts as an additional dynamic pressure element. Two-dimensional pressure sensor array 33 is mounted in holder 12, as shown in FIG. 3.

Disposable polymer films covering the superior and inferior aspects of breast 8 from above and below are replaced after each examination. The surface of these films facing the dynamic pressure of the element (linear pressure sensor array 14 or the roller 31) is covered with lubricant to decrease friction while moving the pressure element over the breast.

FIGS. 3 and 4 illustrate mechanical scanning unit 13 in detail. Rotation unit 25 comprises 5 rollers 31, 34, 35, 36, 37. Each roller 31, 34, 35, 36 is supported by two bearings 46 (see FIG. 4) mounted into the corresponding side supports 42. Linear motion of pressure sensor array 14 connected to slider 39 is accomplished by sliding slider 39 along guide axes 38. Guide axes 38 are attached into side supports 42. Motor 44 controls back-and forth motion of slider 39. The torque of motor 44 is transferred through gear wheels 45, wheel 54 and belt 40 to slider 39. Guide axes 38 are attached into side supports 42. Motor 44 is mounted to side support 42 by means of motor holder 47.

Holder 12 mounts two dimensional pressure sensor array 33, as shown in FIG. 3. Each pressure sensor of two-dimensional pressure sensor array 33 comprises flexible support 48 and PVDF film 49. PVDF film 49 has a metallization on the top surface and flexible support 48 has metallization on the surface which is in contact with PVDF film 49 to collect the charge generated by PVDF film 49 and to transfer it to the electronic circuit. A force applied to sensing tip 50 causes flexible support 48 to flex. This flexion in turn creates high tangential forces in PVDF film 49. A row of pressure sensors 51 forms linear array 52. Linear array 52 can be part of the printed circuit board having electronic components 53 to process the signal generated by PVDF film 49. Two-dimensional pressure sensor array 33 comprises several linear arrays 52 mounted in holder 12.

Referring to FIG. 4, the three-dimensional space motion of linear pressure sensor array 14 is accomplished with vertical linear actuator 21, horizontal linear actuator 23 connected to slider 55 of vertical linear actuator 21, and linear pressure sensor array 14 connected to slider 56 of the actuator 23. Connective pipe 57 extends from support 27 for air supply into airbag 22. Cable 58 provides an electrical connection of linear pressure sensor array 14. Cable 58 can be a flat flexible cable.

Figure 5B:
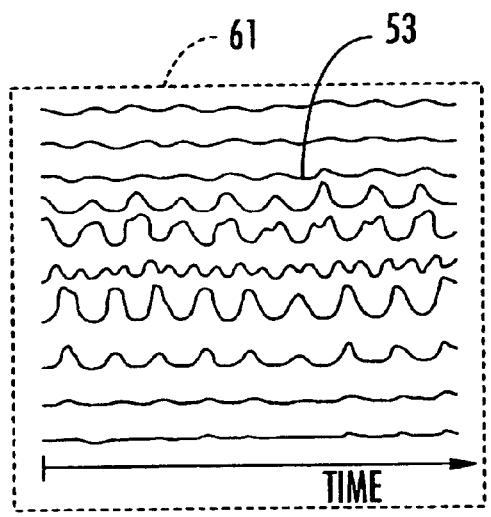
FIG. 5B is a graphical representation of pressure signals for the linear pressure sensor array and the two-dimensional pressure sensor array shown in FIG. 2 obtained by the apparatus of FIG. 4 using the model experiment of FIG. 5A.
Figure 5C:
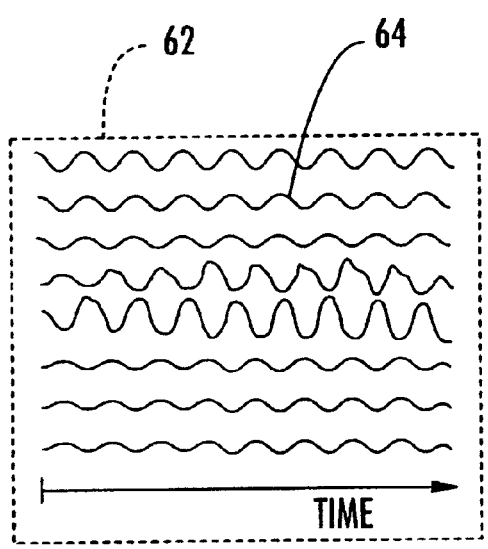
FIG. 5C is a graphical representation of pressure signals for the linear pressure sensor array and the two-dimensional pressure sensor array shown in FIG. 3, obtained by the apparatus of FIG. 4 using the model experiment of FIG. 5A.
Figure 5A:
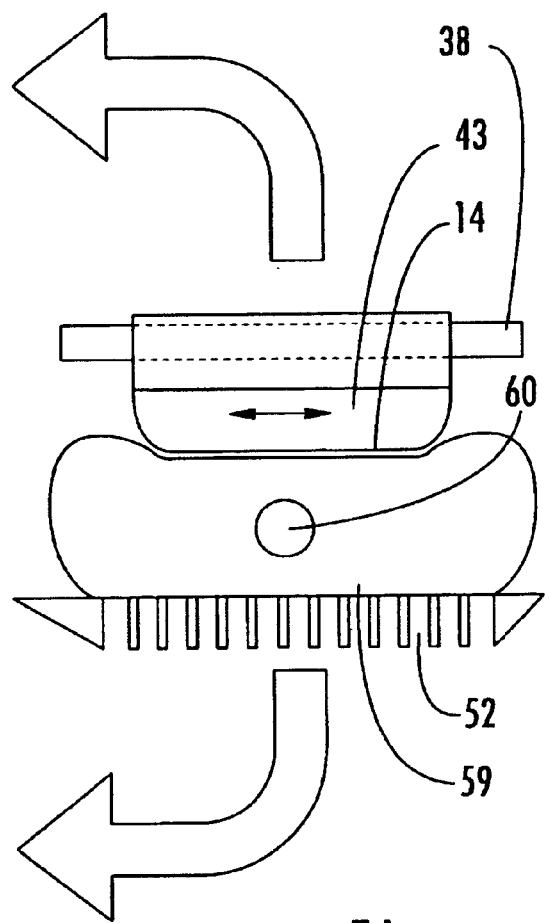
FIG. 5A is a schematic diagram of a model experiment on breast phantom with a hard nodule.

FIG. 5A illustrates linear pressure sensor array 14 pressed against a tissue phantom 59 with a hard inclusion 60. Oscillating linear pressure sensor array 14 over tissue phantom 59 enables detecting the hidden nodules and evaluating parameters for example: the diameter, hardness and depth. Frames 61 and 62, shown respectively in FIG. 5B and FIG. 5C, are the graphical representation of the temporal dependence of signals 63 from linear pressure sensor array 14 as well as temporal dependence of signals 64 from one row of sensors of two-dimensional pressure sensor array 33 during oscillation of the respective linear pressure sensor array. The difference in time profiles of signals from the sensors located at different positions with regard to the nodule, as seen in records 61 and 62, allows detecting and evaluating parameters of the nodules.

Figure 6:
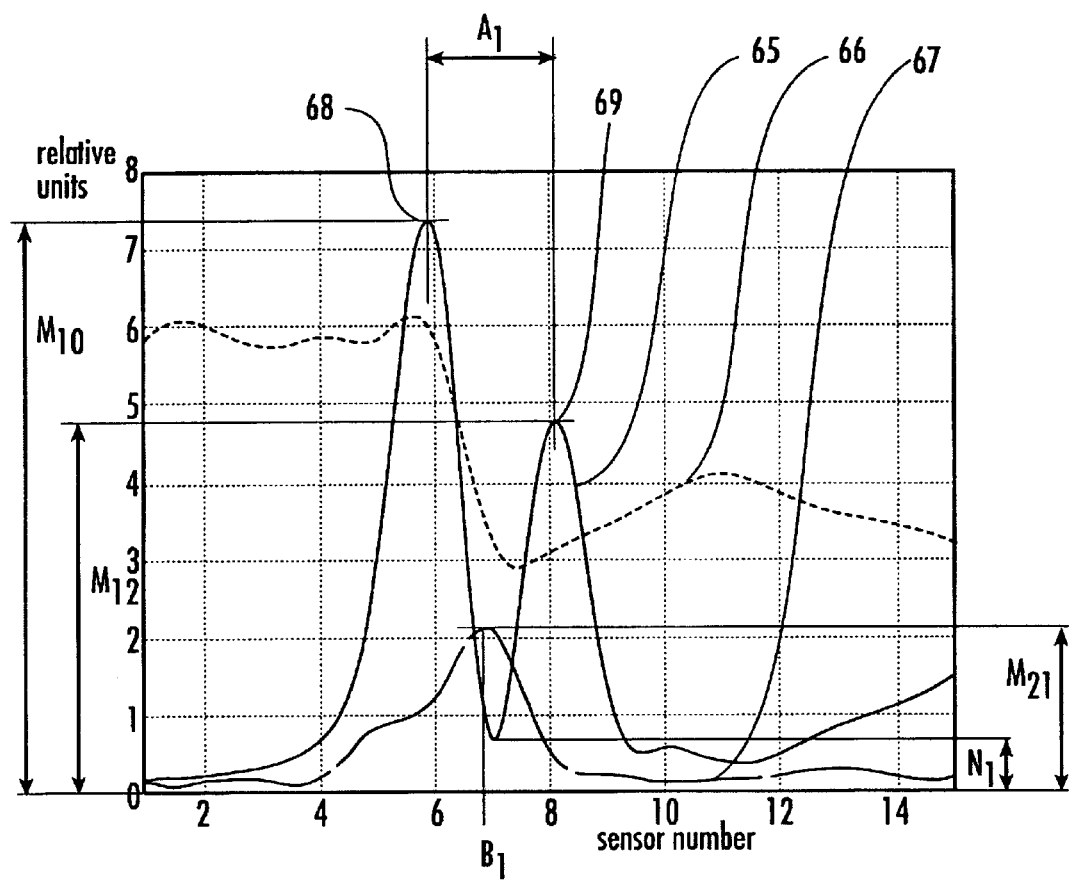
FIG. 6 is a graphical representation of amplitude of the first harmonic, amplitude of the second harmonic and a phase shift of the first harmonic for the pressure signals from the linear pressure sensor array calculated from the experimental data of FIGS. 5A and 5B.

FIG. 6 is a graphical representation of the amplitude of first harmonic 65, amplitude of second harmonic 67 and of phase shift 66 for data of frame 61, shown in FIG. SB. Presence of the nodule produces two distinctly expressed peaks 68 and 69. Parameters $M_{10}$, $M_{12}$, $M_{21}$, $N_1$, $A_1$, and $B_1$ can be used for tissue characterization in order to find all parameters of hard inclusion.

Figure 7A:
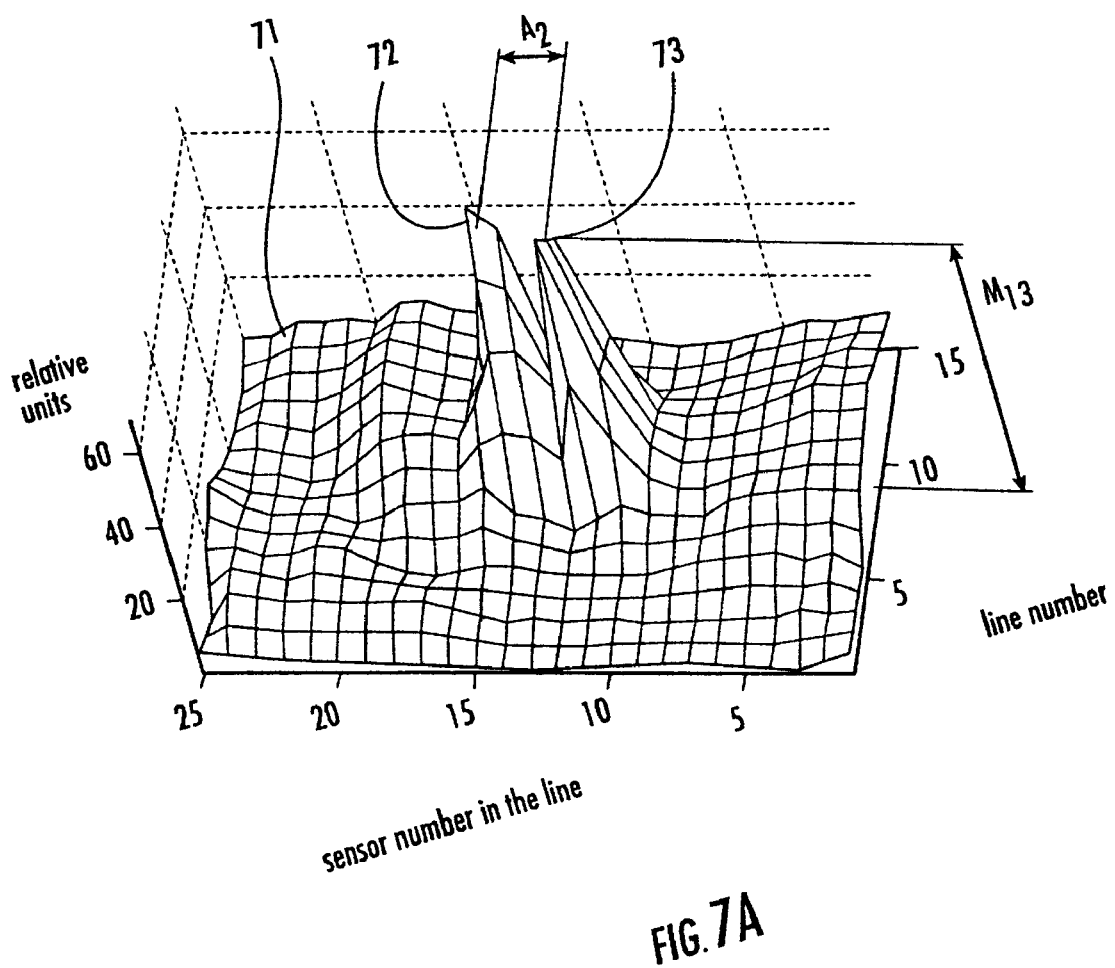
FIG. 7A is a graphical representation of amplitude of the first harmonic for pressure signals from the two-dimensional pressure sensor array calculated from the experimental data of FIGS. 5A and 5B.

FIG. 7A is a 3D graphical representation of the amplitude of first harmonic 71 for pressure signals from two-dimensional pressure sensor array 33 shown in FIG. 3 for the data of frame 62 shown in FIG. 5C. Hard inclusion is located between two peaks 72 and 73. The peak amplitudes $M_{13}$ and distance between them $A_2$ characterize the inclusion.

Figure 7B:
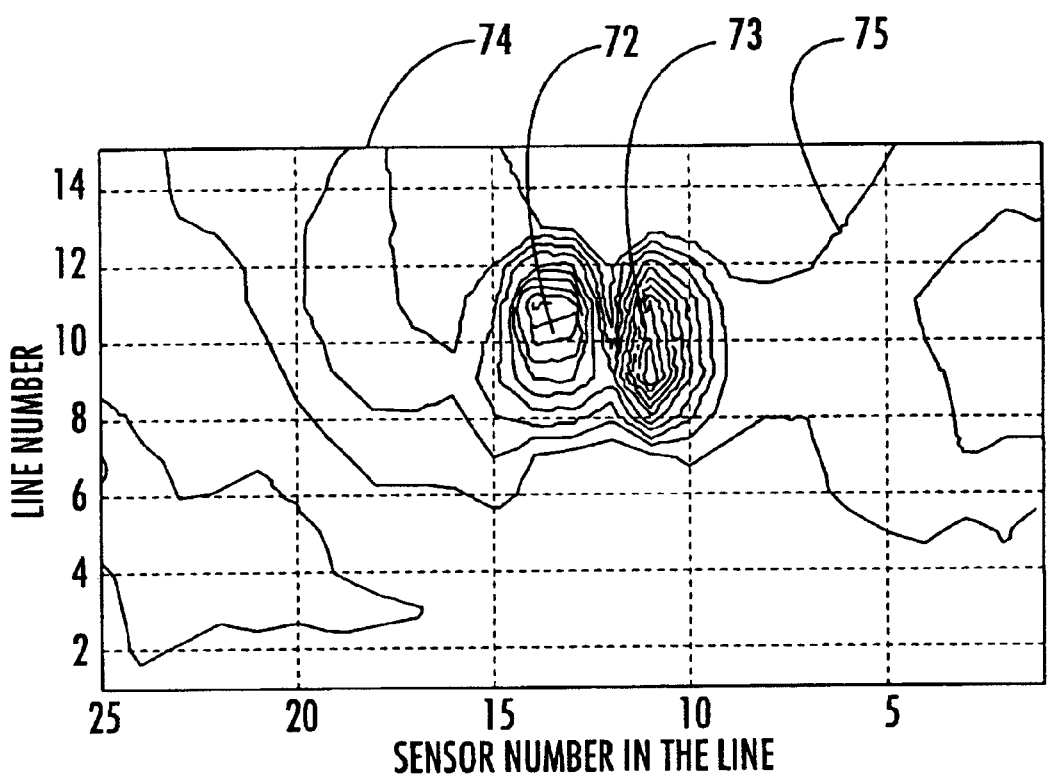
FIG. 7B is a topographic representation of the data shown in FIG. 7A.

FIG. 7B is a topographic representation 74 with lines of equal level 75 for the data shown in FIG. 7A.

Figure 8A:
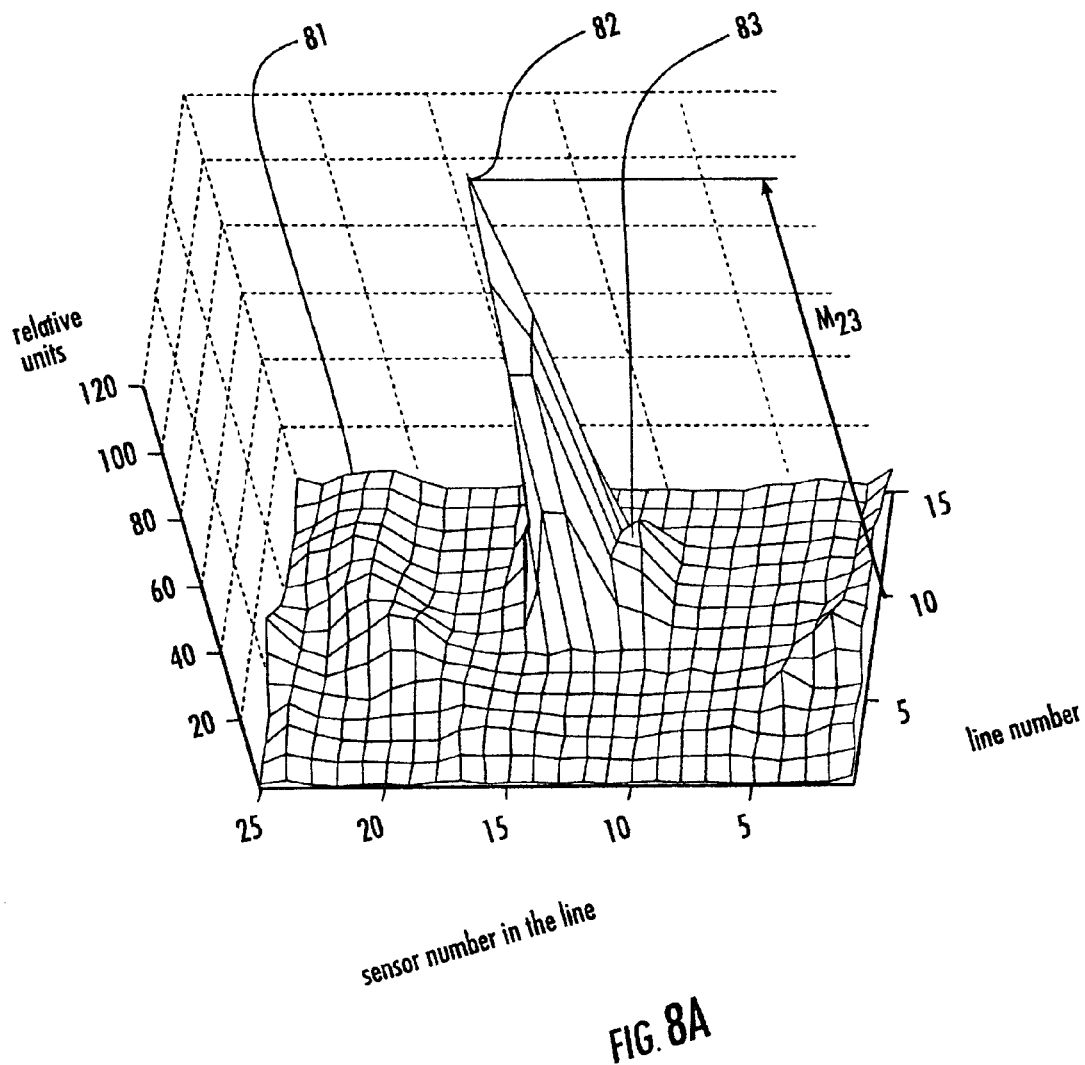
FIG. 8A is a graphical representation of amplitude of the second harmonic for pressure signals from two-dimensional pressure sensor array calculated from the experimental data of FIGS. 5A and 5B.
Figure 8B:
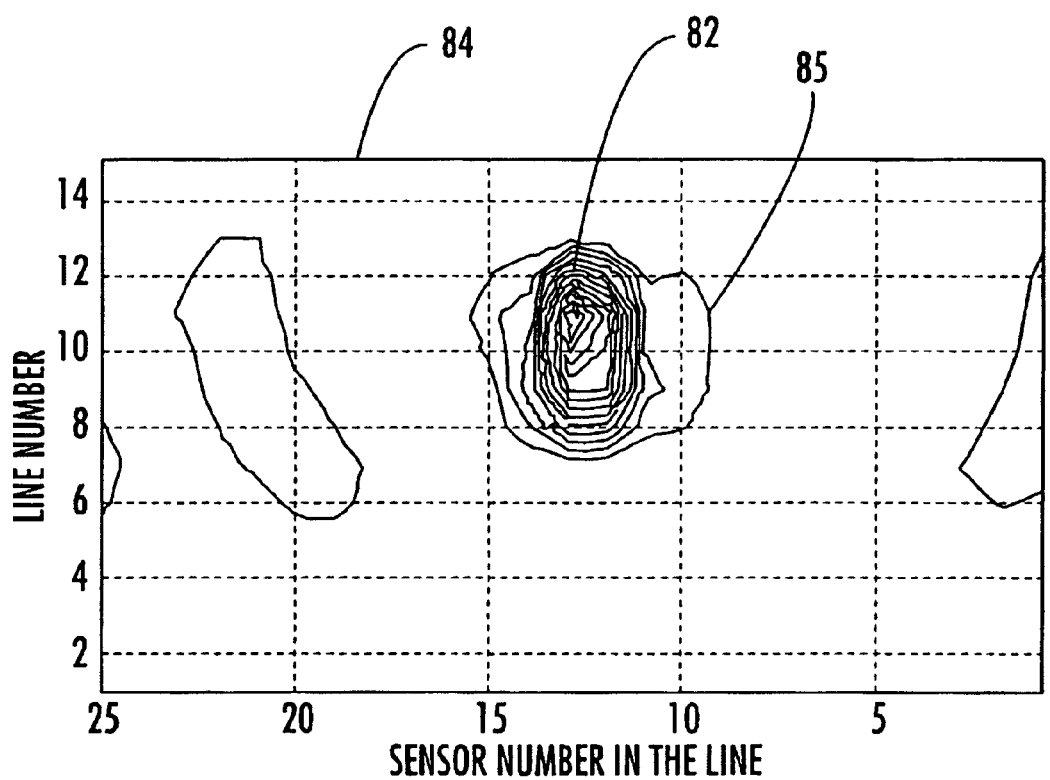
FIG. 8B is a topographic representation of the data shown in FIG. 8A.

FIG. 8A is a 3D graphical representation of the amplitude of second harmonic 81 for pressure signals from the two-dimensional pressure sensor array 33 shown in FIG. 3 for the data shown in FIG. 5C. The inclusion is located under peak 82. Two additional peaks 83 with smaller amplitude may arise in the vicinity of peak 82. The peak amplitude $M_{23}$ characterizes the inclusion. FIG. 8B is a topographic representation 84 with lines of equal level 85 for the data shown in FIG. 8A.

Figure 9A:
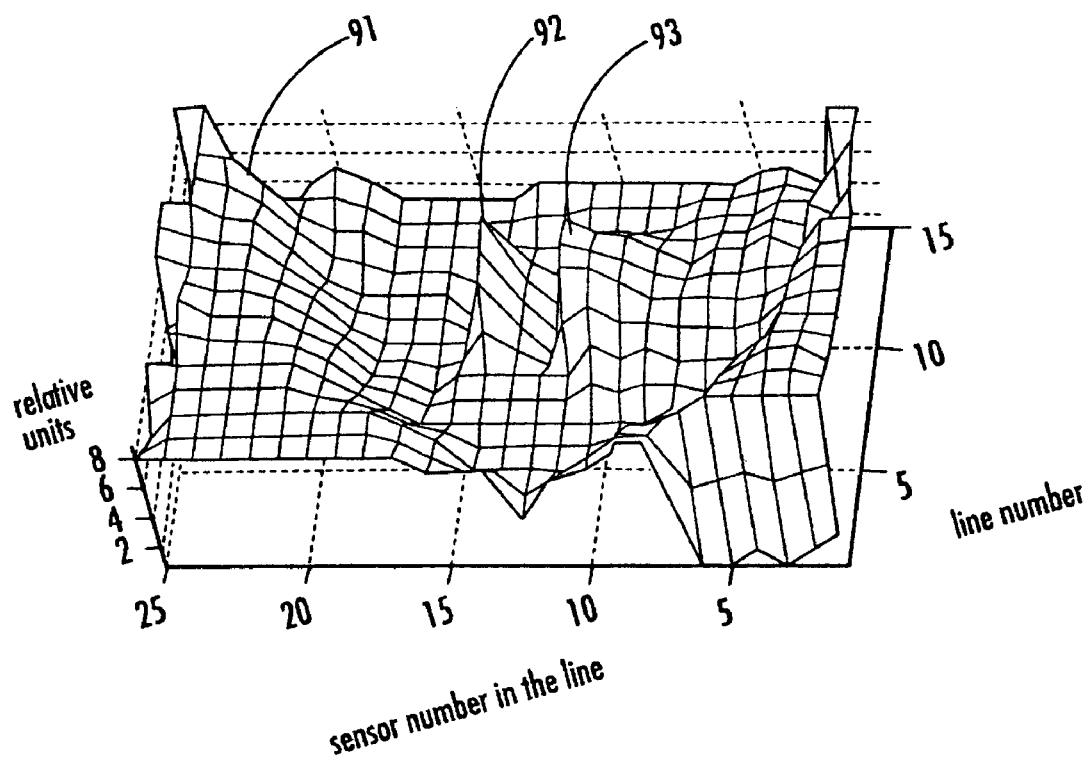
FIG. 9A is a graphical representation of a phase shift of the second harmonic for pressure signals from the two-dimensional pressure sensor array calculated from the experimental data of FIGS. 5A and 5B.
Figure 9B:
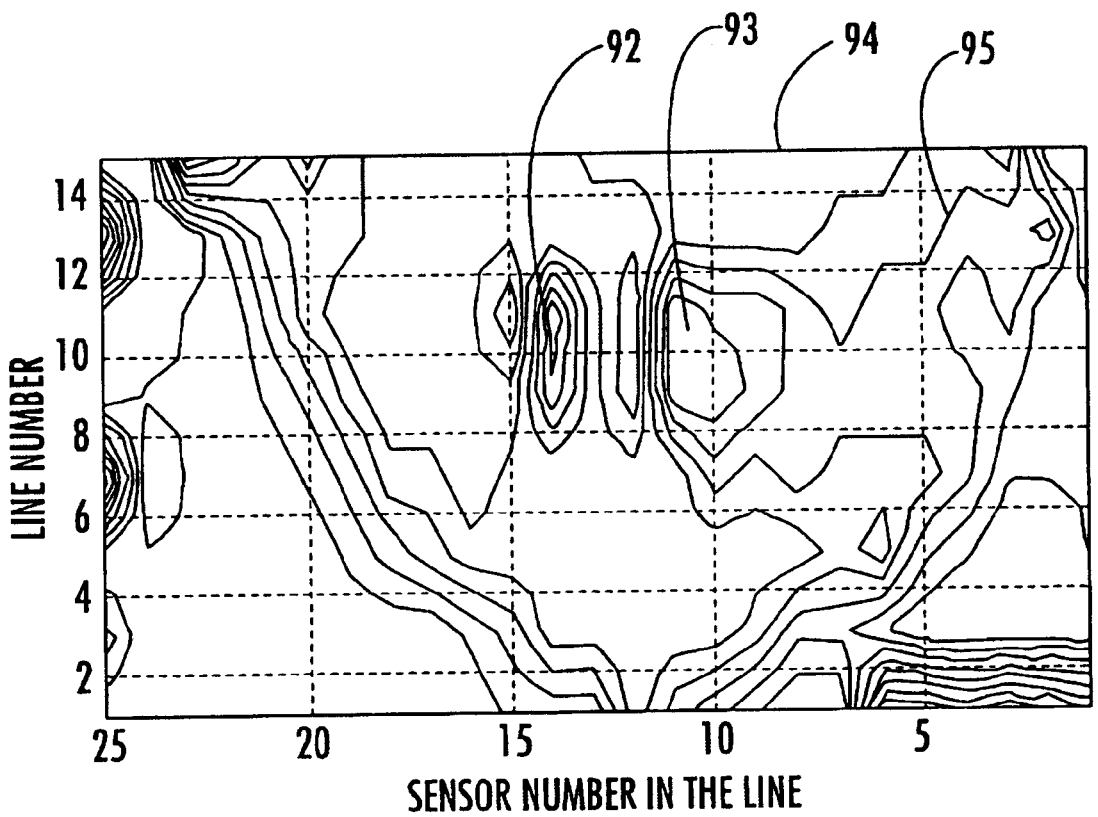
FIG. 9B is a topographic representation of the data shown in FIG. 9A.

FIG. 9A is a 3D graphical representation of a phase shift of second harmonic 91 for pressure signals from the two-dimensional pressure sensor array 33 shown in FIG. 3 for the data given in FIG. 5C. The inclusion is located close to a characteristic peak 92. Additional peak 93 may arise in the vicinity of peak 92. FIG. 9B is a topographic representation 94 with lines of equal level 95 for the data shown in FIG. 9A.

Figure 10A:
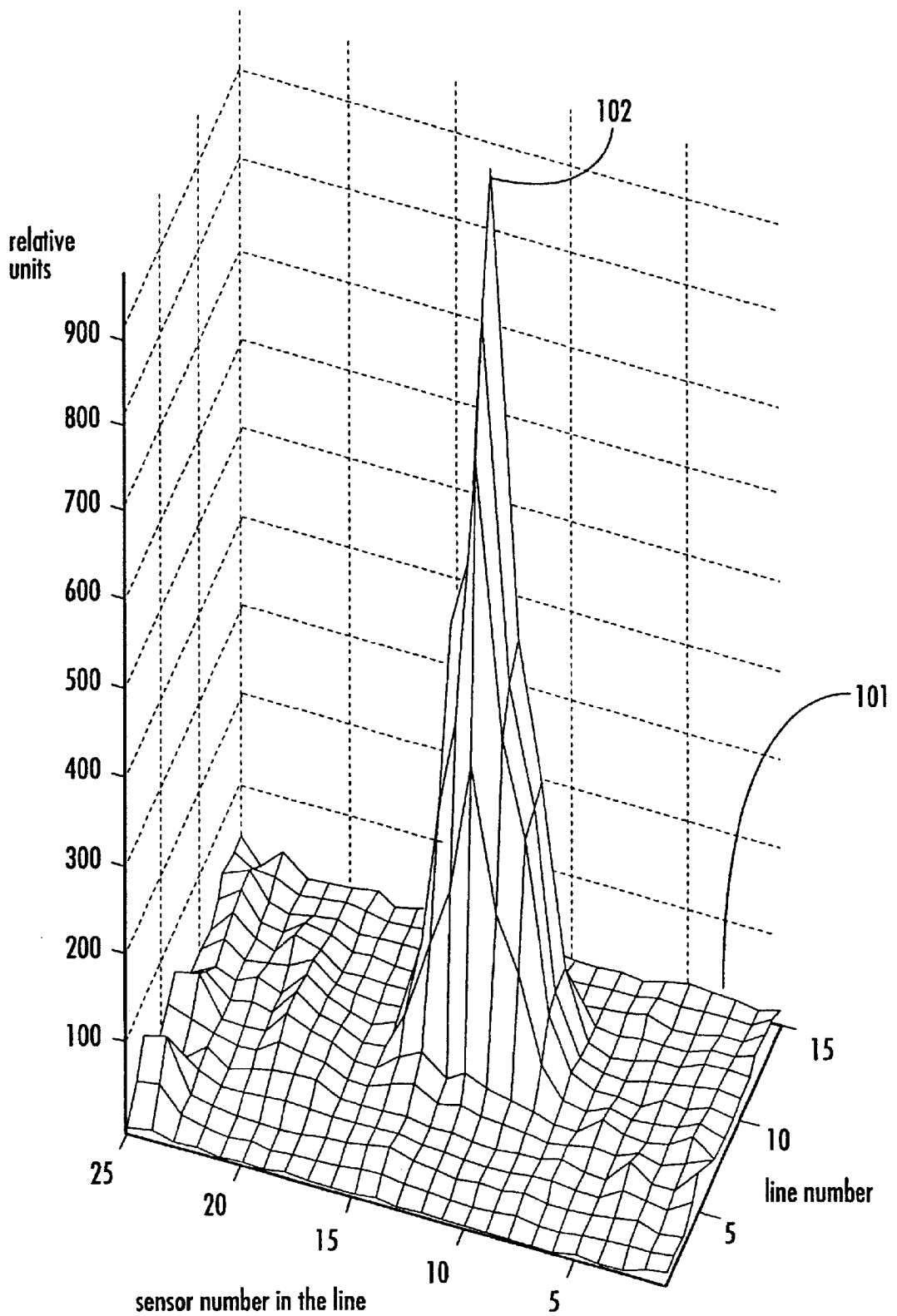
FIG. 10A is a graphical representation of a combined gradient along a sensor line for pressure signals from the two-dimensional pressure sensor array calculated from the experimental data of shown in FIGS. 5A and 5B.
Figure 10B:
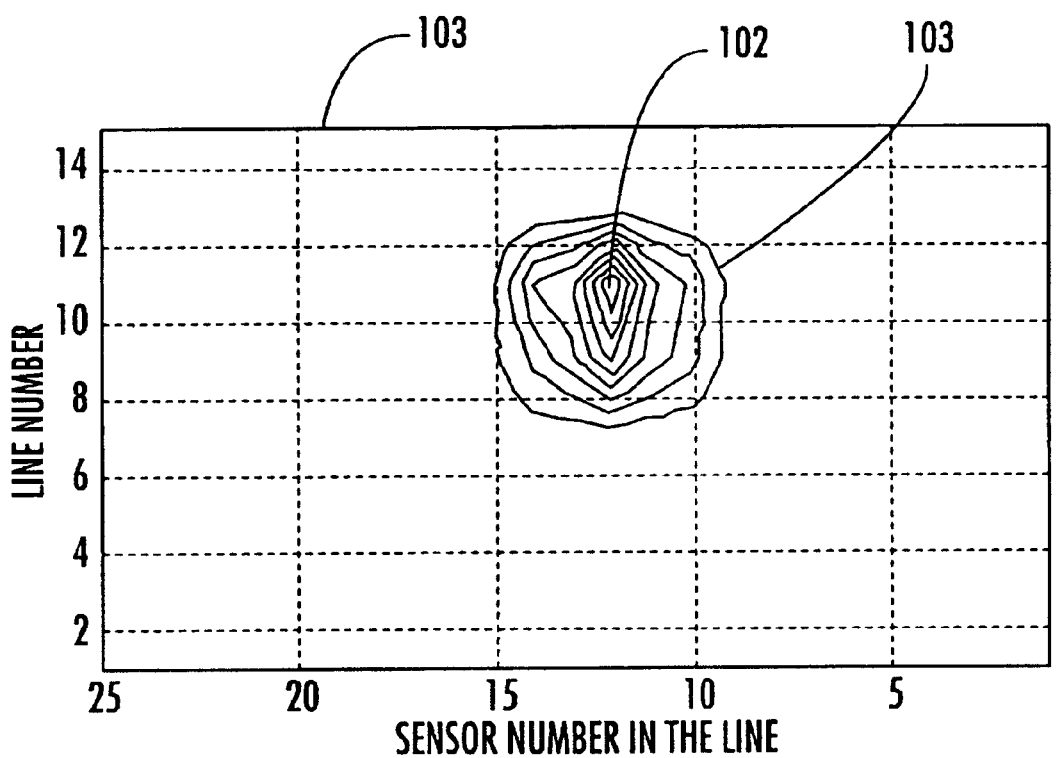
FIG. 10B is a topographic representation of the data shown in FIG. 10A.

FIG. 10A is a 3D graphical representation of a combined gradient 101 along a sensor line 52 for pressure signals from the two-dimensional pressure sensor array shown in FIG. 5C. The inclusion is located under a peak 102. This procedure produces a higher signal/noise ratio and the nodule is detected without any ambiguity. FIG. 10B is a topographic representation 94 with lines of equal level 103 for the data shown in FIG. 10A.

Figure 11:
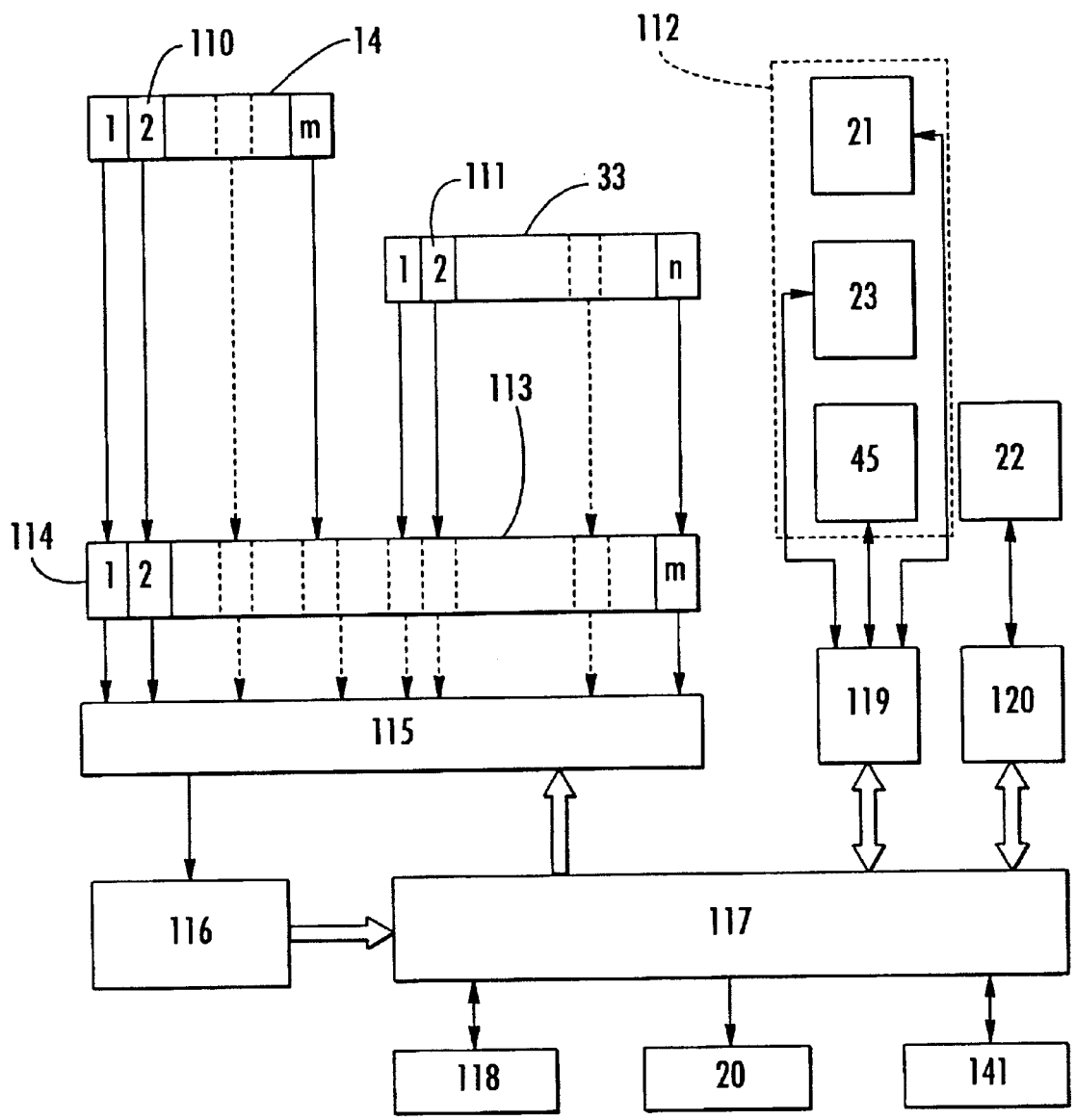
FIG. 11 is a schematic diagram of an electronic unit for controlling mechanical scanning, data acquisition, processing and displaying mechanical images of the breast for the clinical apparatus shown in FIG. 4.

FIG. 11 is a schematic diagram of a preferred embodiment of electronic unit 109 for providing acquisition, scanning, processing and displaying the breast mechanical imaging data for the device shown in FIG. 1. A plurality of transducer elements 110 form pressure sensor array 14 of device 10. A plurality of transducer elements 111 form two-dimensional pressure sensor array 33 of device 10. Pressure sensing circuit 113 is formed of several amplifiers 114 to enhance respective signals generated by pressure transducer elements 110 and 111, for detecting the forces applied to each transducer element 110 of pressure sensor array 14 and each transducer element 111 of pressure sensor array 33. The amplified signals from amplifiers 114 are applied to multiplexer 115. Multiplexed signals are converted to digital signals by the analog-to-digital converter 116 and are fed to processor 117. Robotic 3D positioning system 112 includes linear actuators 21, 23 and rotation actuator 45 connected through controller 119 to processor 117. Controller 120 is connected to processor 117 and controls air pressure in airbag 22. Processor 117 is used to provide all required robotic manipulations of mechanical 13 scanning unit, to control the breast compression and position of each pressure sensing transducer 110, to synchronize and filtrate pressure data received from linear pressure sensor array 14 and two-dimensional pressure array 33. Processor 117 is also used for analysis of mechanical images of the breast, for delineating geometrical features and mechanical composition of the breast, such as lesions, nodules, stiffer tissue, and the like and for synthesis of the breast image, as described in the method illustrated in FIG. 12. Computer display 20 connected to processor 117 displays the process of breast examination and the results of the examination. Control unit 141 is connected to processor 117 for controlling the breast examination, data analysis and data display. Processor 117 communicates with analog-to-digital converter 116 and multiplexer 115 for sending data and control signals. A storage unit 118 is used for storing the results of the breast examination generated by the processor 117 and communication with the patient's database.

Figure 12:
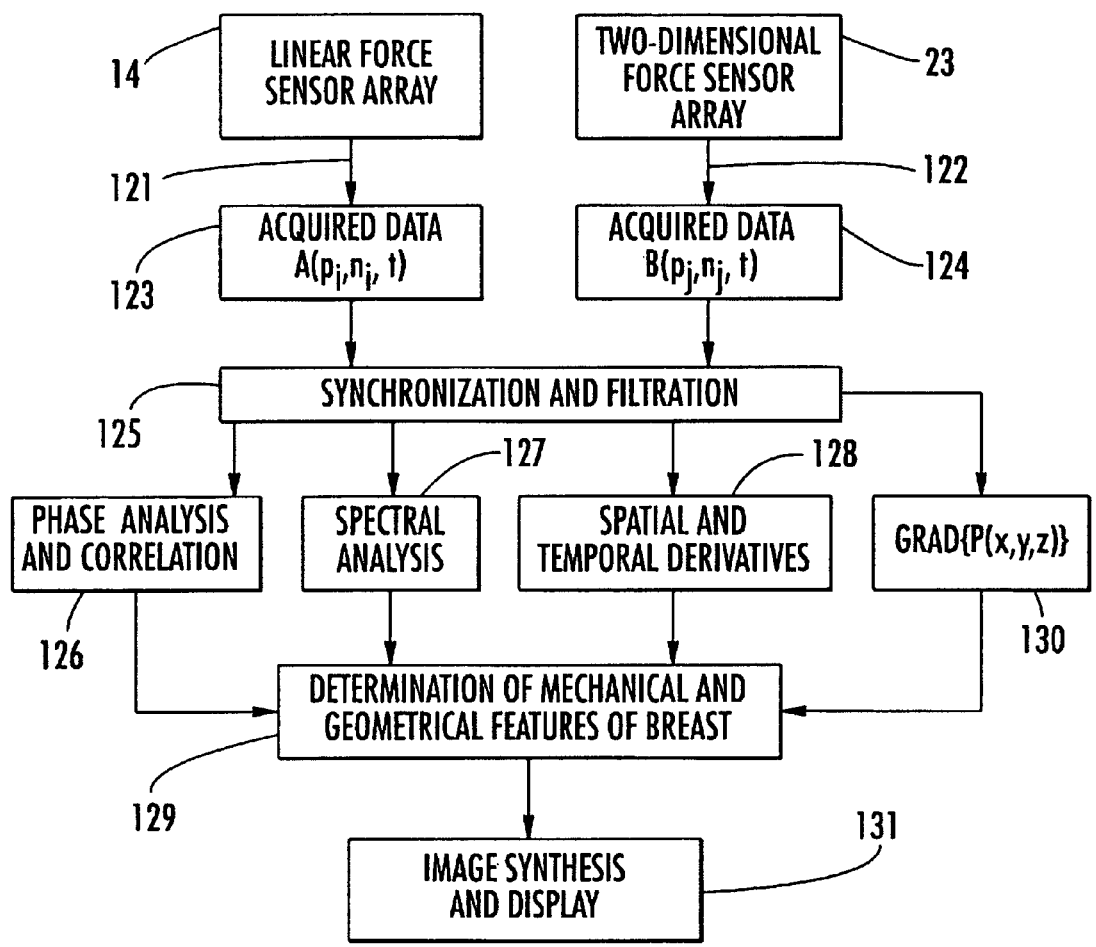
FIG. 12 shows a flow chart representative of an algorithm for determining diagnostic information from the mechanical imaging data in accordance with the present invention.

FIG. 12 shows a flow chart representative of the preferred method and algorithm for analysis of information obtained by scanning the breast. Force data 121 from pressure sensor array 14 and data 122 from pressure sensor array 33 are acquired in real-time. Analog signals representing the force measured from all the force transducers of pressure sensor array 14 at the time t form force data 123 represented by $A(p_i,n_i,t)$, where $p_i$ is the pressure signal from of the pressure transducer $n_i$. Analog signals representing the force measured from all the force transducers of two-dimensional pressure sensor array 33 at the time t form force data 124 represented by $B(pj,nj;t)$, where pj is the pressure signal from the pressure transducer $n_j$. In block 125 the acquired force data 123 and force data 124 are combined over a period of time to conduct synchronization and filtration. In box 125 data are processed by one of the known approximation and filtration method, as described for example by J.-L. Stark, F. Murtagh and A. Bijaouiet, *Image Processing and Data Analysis*. Cambridge University Press (1998). In block 126, corrected data is determined for correcting displacement and shifting of the breast during examination and correcting noise of various origins. Pressure field data is calculated by processing the transformed data to minimize noise and extract the 3D spatial distribution of pressure approximating ideal conditions of measurement. In block 127, spectral analysis is used to analyze the data. In block 128, spatial and temporal derivatives are used to analyze the data. The phase correlations, spectral composition of the signals, and spatial and temporal derivatives of the signals are evaluated and forwarded to the block 129 for evaluating mechanical and geometrical features of the breast. In block 130, a pattern of pressure gradient responses is determined from force sensor array data. Various methods may be used to determine the pressure gradient responses grad$\{P(x,y,z)\}$. One method is calculating partial derivatives for a given pattern of pressure responses along array 52 to locate areas of hardness in the breast. Having approximated surfaces of equal pressure one can calculate geometrical parameters and hardness of the breast in local regions. In block 131 a breast image is synthesized from the data generated in the block 129. The breast examination and the synthesized image of the breast are displayed on computer display 20.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A breast examination device comprising:

a scanning housing receiving a breast;

a linear pressure sensor array formed of a plurality of first sensors and a two-dimensional pressure sensor array formed of a plurality of second sensors, each of said first sensors and said second sensors producing a signal in response to pressure imposed on said respective sensor as said first sensors and said second sensors are pressed and moved against the breast tissue in a pre-determined manner, said linear pressure sensor array and said two dimensional pressure array being coupled to said scanning housing;

a robotic positioning system coupled to said scanning housing for positioning said linear pressure sensor array integrated with a compression mechanism for mechanical compression and a scanning unit for scanning of the breast located inside said scanning housing;

a positioning system for linear and rotary displacement of said scanning housing; and an electronic unit for providing acquisition, scanning, processing and displaying of mechanical imaging data from said first sensors and said second sensors, wherein said linear pressure sensor array comprises plurality of flexing diaphragms positioned in a cylinder filled with an elastic compound and strain gages bonded to an inner side of said flexing diaphragms.

2. A breast examination device comprising:

a scanning housing receiving a breast;

a linear pressure sensor array formed of a plurality of first sensors and a two-dimensional pressure sensor array formed of a plurality of second sensors, each of said first sensors and said second sensors producing a signal in response to pressure imposed on said respective sensor as said first sensors and said second sensors are pressed and moved against the breast tissue in a pre-determined manner, said linear pressure sensor array and said two dimensional pressure array being coupled to said scanning housing;

a robotic positioning system coupled to said scanning housing for positioning said linear pressure sensor array integrated with a compression mechanism for mechanical compression and a scanning of the breast located inside said scanning housing, said robotic positioning system comprises a plurality of linear actuators and rotary actuators to provide three-dimensional motion of said linear pressure sensor array;

a positioning system for linear and rotary displacement of said scanning housing; and and an electronic unit for providing acquisition, scanning, processing and displaying of mechanical imaging data from said first sensors and said second sensors, wherein said compression mechanism comprises:

an airbag mounted on a support connected to one of said linear actuators;

a pressure controller to maintain a predetermined pressure in said airbag; and a holder for holding said two-dimensional pressure sensor array.

3. The breast examination device of claims 2 wherein said scanning unit is located between said airbag and said holder.

4. A breast examination device comprising:

a scanning housing receiving a breast;

a linear pressure sensor array formed of a plurality of first sensors and a two-dimensional pressure sensor array formed of a plurality of second sensors, each of said first sensors and said second sensors producing a signal in response to pressure imposed on said respective sensor as said first sensors and said second sensors are pressed and moved against the breast tissue in a pre-determined manner, said linear pressure sensor array and said two dimensional pressure array being coupled to said scanning housing;

a robotic positioning system coupled to said scanning housing for positioning said linear pressure sensor array integrated with a compression mechanism for mechanical compression and a scanning unit for scanning of the breast located inside said scanning housing;

a positioning system for linear and rotary displacement of said scanning housing; and an electronic unit for providing acquisition, scanning, processing and displaying of mechanical imaging data from said first sensors and said second sensors, wherein said scanning unit comprises:

a plurality of rollers, at least one of said rollers is pressed against the breast and used for total scanning of the breast by means of linear motion of said scanning unit;

a head coupled to said linear pressure sensor array providing oscillating scanning of the breast by means of back-and-forth motion along a predetermined axis and moving up and down against the breast; and a rotary actuator with at least two predetermined positions for changing the pressing of said linear pressure sensor array against the breast.

5. A method for mechanical imaging the breast comprising the steps of:

placing the breast into a scanning housing of a breast examination device, said breast examination device comprising a scanning housing receiving the breast;

a linear pressure sensor array formed of a plurality of first sensors and a two-dimensional pressure sensors array formed of a plurality of second sensors, each of said first sensors and said second sensors producing a signal in response to pressure imposed on said respective sensor as said first sensor and said second sensor are pressed and moved against the breast tissue in a pre-determined manner, said linear pressure sensor array and said two dimensional pressure array being coupled to said scanning housing;

a robotic positioning system for positioning said linear pressure sensor array integrated with a compression mechanism for mechanical compression and a scanning unit for scanning of the breast located inside said scanning housing coupled to said scanning housing; said compression mechanism comprising:

an airbag mounted on a support connected to one of said linear actuators;

a pressure controller to maintain a predetermined pressure in said airbag; and a flat holder for holding said two-dimensional pressure sensor array;

compressing the breast by means of lowering said scanning unit towards the breast and following increase of pressure in said airbag;

scanning of the breast by means of linear movement of in said scanning unit;

scanning of the breast by means of a local oscillatory deformation of the breast tissue portion by said linear pressure sensor array being pressed against that tissue portion; and acquiring pressure response data of said linear pressure sensor array and said two-dimensional pressure sensor array during the said scanning steps.

6. The method of claim 5 further comprising:

repeating said oscillatory deformation over a plurality of the breast tissue portions;

and detecting oscillatory signal from said first sensors.

7. The method of claim 6 further comprising:

synchronizing and filtrating pressure response data from first sensors and said second sensors.

8. The method of claim 7 further comprising;

correcting displacement and shifting of the breast during examination;

correcting noise of said signals and of said first sensors and said second sensors;

analyzing spectral and phase characteristics of said pressure response data; and analyzing spatial and temporal derivatives of said pressure response data.

9. The method of claim 8 further comprising the steps of:

evaluating type and degree of mechanical heterogeneity of the examined breast; and evaluating deviation of the type and degree of mechanical heterogeneity of the breast from the normal range of mechanical heterogeneity of the breast.

10. The method of claim 8 further comprising the steps of:

calculating a pattern of pressure responses and pressure gradient responses of the breast from said pressure response data;

calculating geometrical parameters and hardness in local regions of the breast;

determining mechanical and geometrical features of the inner structures of the breast; and comparing said mechanical and geometrical features to a normal state of the breast using information from a database.

11. The method of claim 5 further comprising the steps of:

synthesizing and displaying a mechanical image of the breast.

* * * * *